(12) United States Patent
Stremmel

(10) Patent No.: US 8,883,426 B2
(45) Date of Patent: Nov. 11, 2014

(54) USE OF THERAPEUTICALLY EFFECTIVE LIPIDS AND METHOD FOR PRODUCING ORGAN-/TISSUE-SPECIFIC THERAPEUTICALLY EFFECTIVE LIPIDS

(75) Inventor: Wolfgang Stremmel, Heidelberg (DE)

(73) Assignee: PAT GmbH, Munich (DE)

( * ) Notice: Subject to any disclaimer, the term of this patent is extended or adjusted under 35 U.S.C. 154(b) by 1125 days.

(21) Appl. No.: 12/052,268

(22) Filed: Mar. 20, 2008

(65) Prior Publication Data

US 2008/0166401 A1 Jul. 10, 2008

Related U.S. Application Data

(63) Continuation of application No. PCT/DE2006/001651, filed on Sep. 18, 2006.

(30) Foreign Application Priority Data

Sep. 21, 2005 (DE) .......................... 10 2005 045 152

(51) Int. Cl.
*G01N 33/53* (2006.01)
*A61K 49/00* (2006.01)
*A61K 47/48* (2006.01)
*A61K 31/685* (2006.01)

(52) U.S. Cl.
CPC ......... *A61K 49/0052* (2013.01); *A61K 49/0021* (2013.01); *A61K 47/48123* (2013.01); *A61K 31/685* (2013.01)
USPC .......................................... 435/7.1; 435/455

(58) Field of Classification Search
None
See application file for complete search history.

(56) References Cited

U.S. PATENT DOCUMENTS

| | | | |
|---|---|---|---|
| 6,677,319 B1 | 1/2004 | Stremmel | |
| 2005/0227925 A1* | 10/2005 | Benner et al. | 514/17 |

FOREIGN PATENT DOCUMENTS

| | | |
|---|---|---|
| EP | 1 105 141 B1 | 11/2003 |
| WO | WO 00/07577 A2 | 2/2000 |
| WO | WO 01/51003 A2 | 7/2001 |
| WO | WO-2004/037275 A1 | 5/2004 |
| WO | WO-2005/084307 A2 | 9/2005 |

OTHER PUBLICATIONS

Paumgartner (Hepatology 2002, vol. 36, pp. 525-531).*

International Search Report for International Appl. No. PCT/DE2006/001651, completed Dec. 12, 2006, mailed Dec. 20, 2006.
International Preliminary Report on Patentability and Written Opinion for International Appl. No. PCT/DE2006/001651, issued Apr. 8, 2008.
Anes, E., et al.; "*Selected lipids activate phagosome actin assembly and maturation resulting in killing of pathogenic mycobacteria;*" Nature Cell Biology, vol. 5, No. 9; pp. 793-802; dated Aug. 2003; abstract retrieved on Feb. 20, 2014 from <http://www.nature.com/ncb/journal/v5/n9/pdf/ncb1036.pdf>.
Fabia, R., et al.; "*Effects of Phosphatidylcholine and Phosphatidylinositol on Acetic-Acid-Induced Colitis in the Rat;*" Digestion, vol. 53, No. 1-2; pp. 35-44; dated 1992; abstract retrieved on Feb. 20, 2014 from <http://www.karger.com/Article/Abstract/200969>.
Lindor, K. D., et al.; *Ursodeoxycholic Acid for Treatment of Nonalcoholic Steatohepatitis: Results of a Randomized Trial;* Hepatology, vol. 39, No. 3; pp. 770-778; dated Mar. 2004.
Milkiewicz, P., et al.; "*Hepatoprotection with tauroursodeoxycholate and β muricholate against taurolithocholate induced cholestasis: involvement of signal transduction pathways;*" Gut, vol. 51, No. 1; pp. 113-119; dated Jul. 2002.
Mourelle, M., et al.; "*Polyunsaturated phosphatidylcholine prevents stricture formation in a rat model of colitis;*" Gastroenterology, vol. 110, No. 4; pp. 1093-1097; dated Apr. 1996; retrieved on Feb. 20, 2014 from <http://www.gastrojournal.org/article/S0016-5085(96)00164-3/abstract>.
Stremmel, W., et al.; "*Retarded release phosphatidylcholine benefits patients with chronic active ulcerative colitis;*" Gut, vol. 54, No. 7; pp. 966-971; dated Jul. 2005; retrieved on Feb. 20, 2014 from <http://gut.bmj.com/content/54/7.toc>.
Office Action for Chinese Application No. 200680037928.0; dated May 12, 2010.
Office Action for European Application No. 06 805 305.7; dated Apr. 15, 2010.
Office Action for German Application No. 10 2005 045 152.7; dated Jun. 30, 2006.

* cited by examiner

*Primary Examiner* — Celine Qian
(74) *Attorney, Agent, or Firm* — Alston & Bird LLP

(57) ABSTRACT

The use of therapeutically active lipids for organ/tissue-specific enrichment for the treatment of inflammatory, ischemic or degenerative disorders and/or for stimulating a regeneration is arranged and developed such that the lipids are bound on application to carrier molecules for which cell-specific uptake systems in the cells of the organs and/or tissue exist. In addition, a method of producing organ/tissue-specific therapeutically active lipids for treatment of inflammatory, ischemic or degenerative disorders and/or stimulation of a regeneration, in particular for treating inflammatory liver disorders, is claimed, which is arranged and developed such that lysophosphatidylethanolamine (LysoPE) is coupled to the carboxyl group of ursodeoxycholate (UrsoDOCA) converted to an ester to give a LysoPE-DOCA compound.

7 Claims, 1 Drawing Sheet

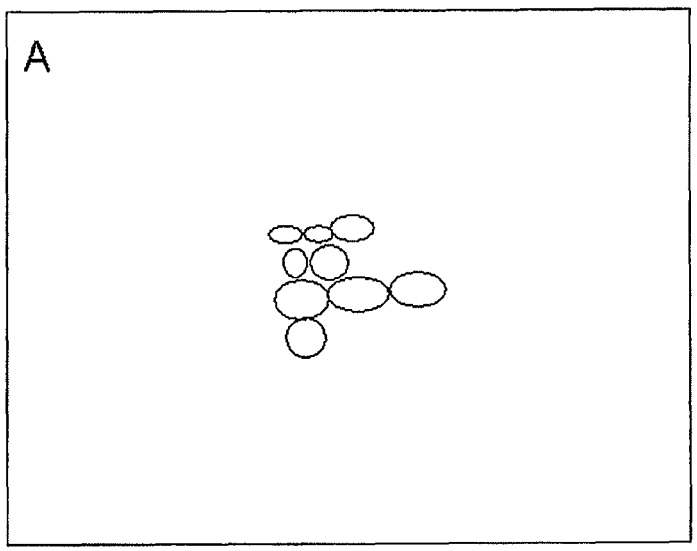
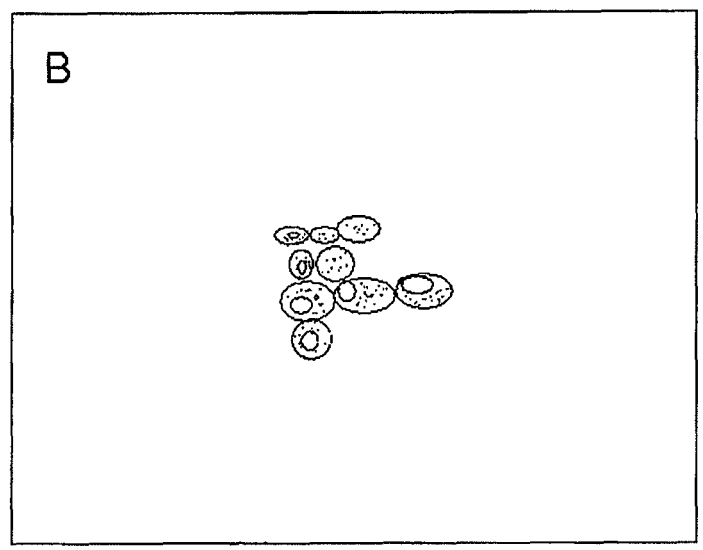

USE OF THERAPEUTICALLY EFFECTIVE LIPIDS AND METHOD FOR PRODUCING ORGAN-/TISSUE-SPECIFIC THERAPEUTICALLY EFFECTIVE LIPIDS

CROSS-REFERENCE TO RELATED APPLICATIONS

The present application is a Continuation of International Application No. PCT/DE2006/001651, filed Sep. 18, 2006, and which designates the U.S. The disclosure of the referenced application is incorporated herein by reference.

FIELD OF THE INVENTION

The present invention relates to the use of therapeutically effective lipids for an organ-/tissue-specific enrichment for treating inflammatory, ischemic, or degenerative diseases and/or for stimulating regeneration. Furthermore, the present invention relates to a method for producing organ-/tissue-specific therapeutically effective lipids for treating inflammatory, ischemic, or degenerative diseases and/or for stimulating regeneration, in particular for treating liver diseases.

BACKGROUND OF THE INVENTION

Certain therapeutically valuable lipids are effective pro-inflammatorily and/or anti-inflammatorily (ANES and coworkers—Nat. Cell. Biol. 2003; 5: 793-802.) In in-vitro models with macrophage models and phagosomes a therapeutic effect of phosphatidyl choline (PC) and lyso-phosphatidyl choline (LysoPC) in an enrichment of these lipids in the respective cells could already be shown on inflammatory activities or a disturbed metabolism (Anes and coworkers—Nat. Cell. Biol. 2003; 5: 793-802.) A therapeutic effect of PC has already been shown in animal models, for example, with the topic application of the anti-inflammatorily effective phosphatidyl choline in rat models protecting colon mucosa from colitis induced by acetic acid and trinitro-benzosulfonic acid (FABIAN et al.—Digestion 1992; 53: 35-44; MOURELLE et al.—Gastroenterology 1996; 110: 1903-7.) Even in humans this principle has been applied for the treatment of the frequently chronic inflammatory intestinal disease colitis ulcerosa. Here, it could be shown that the oral administration of phosphatidyl choline in a retarding packaged form with a release in the lower small intestine and the colon significantly suppresses the inflammatory activity of colitis ulcerosa (STREMMEL et al.—Gut 2005; 54: 966-997, European patent 1 105 141 B1). Compared to a control group treated with placebo an improvement of the clinical activity on average by 70% could be achieved in 90% of the patients treated with PC. Within three months more than half of the patients reached even clinical remission. Simultaneously the endoscopic findings and the histology in the lower small intestines and the colon improved as well as the quality of life of the patient.

Based on the existing results it is probable that diseases of other cells, tissues, and organs in addition to the small intestine and the colon associated with inflammation could be treated with anti-inflammatorily effective lipids. However, it cannot be expected that the systemic unselective administration of phosphatidyl choline, for example, achieves the necessary anti-inflammatory effective level on site, thus local application is required. For example, in local, inflammatorily caused conditions anti-inflammatory lipids per se can be applied locally, such as, e.g., in the topical administration of inflamed skin areas, the instillation in joint cavities for arthritis, the inhalation of suitable preparations into the bronchial system for treating pneumonia, or in the instillation of lipid suspensions into the gastro-intestinal tract, e.g., the esophagus, the stomach, the duodenum, and the rectum.

The local application in parenchymatous organs, such as liver, hearth, and brain presents a more difficult problem. Here, in order to achieve a high local concentration in these organs a local infusion of therapeutically effective lipid suspensions or the use of reversible embolisation techniques could occur, however, no real alternatives develop for the local application with regard to the duration of the infusion and the risks to be feared by the application of embolisation techniques.

SUMMARY OF THE INVENTION

The present invention is therefore based on an object of providing a use of therapeutically effective lipids for an organ-/tissue-specific enrichment for treating inflammatory, ischemic, or degenerative diseases and/or for stimulating regeneration of the type mentioned at the outset for all organs, tissues, and cells excluding risks and long-term infusions, leading to a therapeutically effective concentration of lipids in the organs, tissues, and cells.

According to the invention the above-mentioned object regarding the use of therapeutically effective lipids for an organ-/tissue-specific enrichment for treating inflammatory, ischemic, or degenerative diseases and/or stimulating regeneration and other objects are attained by providing a method comprising applying therapeutically effective lipids, wherein during application the lipids are bonded to carrier molecules, for which cell-specific absorption systems exist in the cells of the organs and/or the tissues. Therefore, the use of therapeutically effective lipids is embodied such that for the application the lipids are bonded to carrier molecules existing for the cell-specific absorption systems in the cells of organs and/or tissues.

Furthermore, the above-mentioned object with regard to a method for producing organ-/tissue-specific therapeutically effective lipids for treating inflammatory, ischemic, or degenerative diseases and/or stimulating regeneration, in particular for treating inflammatory liver diseases, is attained by providing a method for producing organ-/tissue-specific therapeutically effective lipids comprising coupling lyso-phosphatidyl ethanolamine (LysoPE) to a carboxyl group of ursodeoxycholate (UrsoDOCA) converted into an ester to form a LysoPE-DOCA-compound. Accordingly, a method for producing organ-/tissue-specific therapeutically effective lipids of the type mentioned at the outset is embodied such that lyso-phosphatidyl ethanolamine (LysoPE) is coupled to a carboxyl group of ursodeoxycholate (UrsoDOCA), converted into an ester, forming a LysoPE-DOCA-compound.

In a manner according to the invention it has been discovered that by the use of lipids bonded to carrier molecules a specific enrichment of these lipids can also be achieved in parenchymatous organs, excluding embolisation or infusion techniques, when cell-, tissue-, or organ-specific absorption systems exist for the carrier molecules. Furthermore, it has been discovered that the cells cannot absorb complex lipids, such as phosphatidyl choline, and thus lyso-phospholipids are coupled to carrier molecules, provably absorbed into the cells. Accordingly, by this cell-specific "targeting" selective absorption of the therapeutically effective lipids is possible into cells, tissues, or organs up to a therapeutically effective concentration. For example, a therapeutically effective concentration of lipids in liver cells showing inflammatory changes can be achieved by lipid compounds produced according to an embodiment of the present invention.

In a particularly advantageous manner the therapeutically effective lipids act anti-inflammatorily or pro-inflammatorily. When the specific enrichment of lipids, procured by the carrier molecules, or by the direct, inhalation, or drop-wise application of the therapeutically effective lipids such as phosphatidyl choline or lyso-phosphatidyl choline (LysoPC) into the cells, tissues, or organs was successful, their anti-inflammatory effect can develop. In addition to the pure substitution of potentially missing lipids the therapeutic effect is additionally provided by an intrinsic anti-inflammatory activity of the lipids by the influence on mediators and signal transmission paths. This way, for example, inflammatory reactions can be treated with the anti-inflammatorily effective lipids, caused as a physiological response to mechanic/degenerative, pathogen-caused, ischemic, free radical-induced, immunologically transmitted, or medication-, drug-, chemical-, or radiation-related damage mechanisms. An immunosuppressive effect is also possible by the absorption of these lipids in macrophages or other cells of the defense and immune system.

The use of pro-inflammatory lipids is indicated particularly in case of intended regeneration. Due to the fact that inflammation (aided by mediators, such as IL6 and TNFα) frequently induces a subsequent regeneration, therapeutically used pro-inflammatory lipids—again topically applied—can be used for promoting regeneration, repair, and hyperplasia of cells, tissues, and organs. For example, the regenerative capacity of the liver can be used in order to subsequently allow increased sectional liver secretion in case of tumors (in other liver segments.) However, this principle applies to other organs as well.

In a particularly advantageous manner the use of pro-inflammatory lipids in organs is particularly preferred in which the cell mass has reached a critical genesis by a chronic disease or accidental/surgery-induced loss. For example, the treatment of short-intestinal syndromes from conditions after resection, cauterized cirrhosis of the liver, ischemia-related myocardial loss, or degenerative diseases of the central nervous system and/or ischemia related loss of parenchyma must be mentioned. Furthermore, the pro-inflammatory lipids can also be used for a treatment to regenerate the immune system and to repopulate the myeloid and lymphoid proliferation systems after chemotherapy and/or radiation or serve to prevent the development of cancer in these organs.

The use of pro-inflammatorily effective lipids is particularly advantageous prior to a planned, extensive partial liver resection, e.g., to remove liver metastases, for inducing sufficient liver cell mass in the remaining liver. For this purpose prior to surgery the pro-inflammatory lipid is selectively instillated in the liver section remaining after surgery.

Furthermore, a pro-inflammatory effect can enhance the immune stimulation in malignant cells and thus be used for anti-tumor therapy (e.g., induction of apoptosis.)

Furthermore, it is advantageous to use ligands, naturally existing in the organism to be treated, as carrier molecules, to which the lipids are covalently bonded. The ligands are recognized according to the cell-specific receptors of the basolateral membrane-associated transport system, via which the lipids can be transferred into the cells. For example, the lipids are bonded covalently to bile acid or asialoglyco-proteins as ligands for a hepatocyte-specific absorption. Particularly the $Na^+$/taurocholate co-transporting polypeptide (NTCP-transporter protein) must be mentioned as a hepatocyte-specific transport system, via which more than 90% of the bile acid is transported into the liver cells.

With regard to the development of an anti-inflammatory or pro-inflammatory effect in the cell the lipids, such as lyso-phosphatidyl choline (LysoPC) or lyso-phosphatidyl ethanolamine (LysoPE) can be released from the ligands after the absorption into the cytoplasm space of the cell. This occurs, for example, by hydrolysis in the cytoplasm. When lyso-phosphatidyl ethanolamine is transported into the cells, as in the above-mentioned case, an enzymatic conversion of the LysoPE into the anti-inflammatorily effective PC occurs after the release of the ligand.

A cardiomyocyte-specific or brain cell-specific enrichment occurs in a beneficial manner via the respective ligand/absorption systems. This way, for example by brain-specific selective enrichment of anti-inflammatory lipids, inflammatory ischemic or degenerative diseases can be treated as well as encephalopathies, such as the hepatic encephalopathy. Furthermore, the selective enrichment of anti-inflammatory lipids in cardiomyocytes in inflammatory areas of the cardiac wall can occur for improving or even preventing severe heart diseases, such as the prevention of a heart attack.

In general, all application paths are available for the use of therapeutically effective lipids, such as the direct, inhalation, drop-wise (instillation), oral, intravenous, or intra-peritoneal application. Here, as described above, particularly suitable is the direct application for the use of anti-inflammatory lipids to treat inflammation-damaged skin or the injection into joints or liquor spaces. The application by inhalation is suitable, for example, for treating an inflammation of the bronchial system, while the enrichment of anti-inflammatory lipids in the gastrointestinal tract or the bladder can occur via instillation. The oral, intravenous, or intraperitoneal application is particularly indicated for the selective enrichment of therapeutically effective lipids in parenchymatous organs, tissues, and cells with inflammatory changes. Here, particularly the intravenous application of lipids bonded to the carrier molecules is suitable because they directly reach the respective organs, tissues, or cells via the blood stream without previously passing through the intestinal wall, as in oral applications, which bears the risk of a complete absorption of the lipids in the intestinal cells.

In addition to inflammatory, ischemic, or degenerative diseases of the liver, the heart, the brain, the skin, the intestine, the joints, and the lung (bronchial system) the use of the therapeutically effective lipids can also occur for the treatment of inflammatory, ischemic, or degenerative diseases of the muscular system, the reticulo-endothelial system (RES), the lymphatic system, endocrinal organs, the peripheral nervous system, the prostate, the bile-duct system, the pancreas, and the bones, etc. The use of therapeutically effective lipids is therefore not limited to special organs, tissues, or cells, but rather can occur for the treatment of all organs, tissues, and cells showing inflammatory changes.

As a whole, the lipid-based therapy described here offers overall good clinical effectiveness with little or no side effects, because it relates to non-immunogenic lipids existing naturally in the organism. This offers the chance to administer locally high dosages of these lipids, with the systemic concentrations remaining within the scope of physiological limits.

BRIEF DESCRIPTION OF THE DRAWINGS

The present invention will be described in more detail hereinbelow with the aid of an exemplary embodiment of the inventive apparatus, with reference to the accompanying drawings.

FIG. 1 shows in the image A the light-microscopic observation of HepG2-cells after an incubation with ursodeoxycholate-1-palmitoyl, 2-NBD-PE-conjugate in a phase contrast, and image B shows the fluorescence-microscopic observation of the cells shown in A.

DETAILED DESCRIPTION OF PREFERRED EMBODIMENTS

Now, there are various ways to embody and beneficially further develop the teaching of the present invention. Here, reference is made to the following description of a preferred exemplary embodiment which explains the claimed method for the production of organ-/tissue-specific therapeutically effective lipids. In the context of the description of the preferred exemplary embodiment generally preferred embodiments and further developments of the teaching are also explained without limiting the teaching thereto.

Example

Exemplary enrichment of anti-inflammatory phospholipids in hepatocytes for suppressing inflammation of the liver.

Complex lipids, such as phosphatidyl choline (PC) per se, cannot be absorbed into the cells. The absorption occurs in the form of lyso-phospholipids which are bonded covalently to a ligand, such as bile acid or asialoglyco-protein, absorbed via bile acid transporters (for example NTCP) at the basolateral plasma membrane of the hepatocytes into the cytoplasm space of the cells. For this purpose, for example lyso-phosphatidyl choline (LysoPC) can be bonded covalently to bile acid, for example to deoxycholate (DOCA.) However, the synthesis of a coupled lysophospholipid-DODC-compound with lyso-phosphatidyl ethanolamine (LysoPE) is chemically much more beneficial. The following reaction can be realized, for example: First the carboxyl group of UrsoDOCA is converted to an active ester by a carbodiimide. Then bonding occurs to LPE. This head-group configuration allows the passage of the LysoPE-DOCA-compound into the liver cells by bile acid transporters. Here, by hydrolytic splitting, LysoPE is released once more, which then is converted enzymatically into the anti-inflammatory PC.

In reference thereto, an acyl-chain conjugation can be performed, in which DOCA is bonded to the acyl side chain of the Sn-1 or Sn-2 position of the PC. Here, after the exposition with phospholipase A2 or A1, the Sn-1 or Sn-2 side group must be converted to an alcohol compound. This is made to bond with an intermediate from the reaction of pyridine with the activated DOCA ester as well as carbodiimide.

The following reaction diagram illustrates the above-described reaction process.

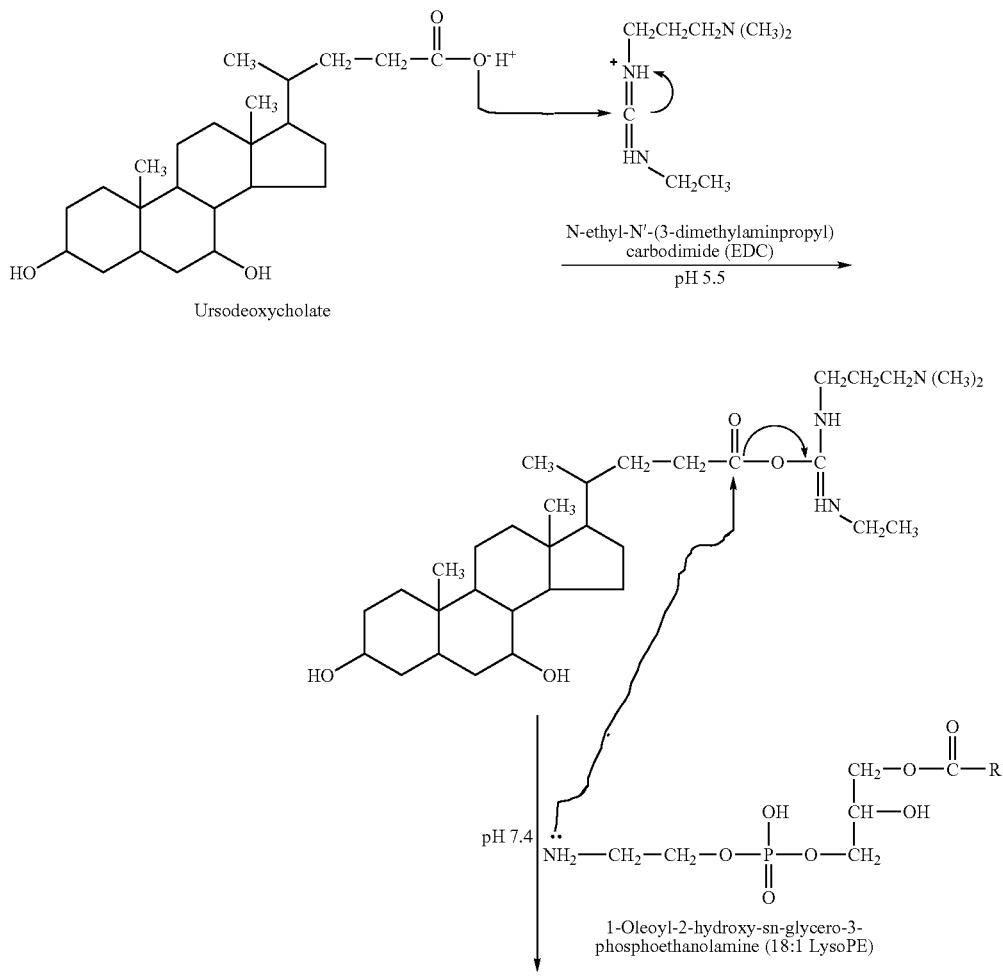

-continued

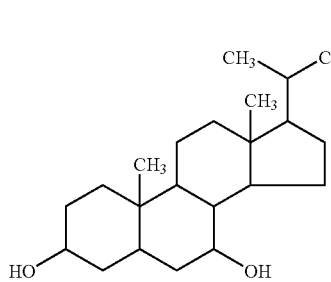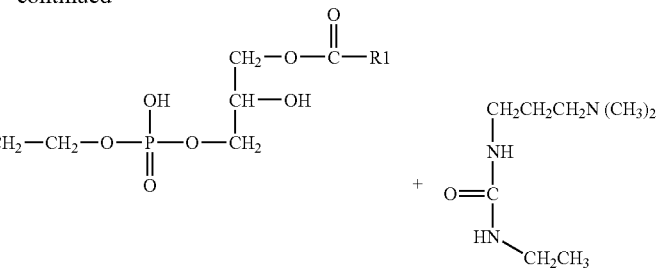

Ursodeoxycholate-18:1 LysoPE conjugate

In order to control the selective enrichment of the LysoPE-DOCA-compound HepG2-cells (hepatocytes) were incubated at 37° C. with a fluorescence-marked ursodeoxycholate-1-palmitoyl, 2-NBD-PE-conjugate (at 50 uM) for 10 min., washed, and subsequently treated with 5% beef-serum albumin in order to remove the conjugate from the exterior plasma membrane of the cells. Subsequently the cells are microscopic controlled in phase contrast and in fluorescent light.

FIG. 1 shows in the image A the light-microscopic observation of HepG2-cells after an incubation with ursodeoxycholate-1-palmitoyl, 2-NBD-PE-conjugate in a phase contrast, and image B shows the fluorescence-microscopic observation of the cells shown in A.

FIG. 1 shows, in image A and image B HepG2-cells (hepatocytes) after the incubation with a therapeutically effective lipid according to the invention (ursodeoxycholate-1-palmitoyl, 2-NBD-PE-conjugate), which is marked with a fluorescent marker to illustrate the enrichment in the cells. In contrast to the HepG2-cells observed in the phase contrast under A, the same cells under fluorescent-microscopic observation show an intense yellow-green coloration in the cytoplasm but not in the core of the cell.

Finally, it is to be specifically pointed out that the above-described example and the FIGURE shown only serve as illustrations of the claimed teaching without limiting it to the example and the FIGURE.

That which is claimed is:

1. A method of treating inflammatory liver diseases and/or to stimulate regeneration of liver organ/tissue cells, said method comprising applying a LysoPE-DOCA-compound to a subject in need thereof.

2. The method according to claim 1, wherein the LysoPE is released from the LysoPE-DOCA-compound after absorption into the cells.

3. The method according to claim 1, wherein the LysoPE-DOCA-compound comprises a hepatocytic-specific ligand specifically recognized and absorbed by an absorption system of the cells of the liver.

4. The method according to claim 3, wherein the absorption system is a $Na^+$/taurocholate co-transporting polypeptide (NTCP-transporter protein.)

5. The method according to claim 1, wherein applying therapeutically effective lipids occurs by at least one of direct, inhalation, drop-wise, oral, intravenous, or intraperitoneal application.

6. A method of selectively enriching a LysoPE-DOCA-compound concentration in liver organ/tissue cells, said method comprising applying a LysoPE-DOCA-compound by at least one of direct, inhalation, drop-wise, oral, intravenous, or intraperitoneal application, wherein the LysoPE-DOCA-compound is selectively absorbed by a cell-specific absorption system of the cells of the liver such that the LysoPE lipid is selectively enriched in the liver organ/tissue, and wherein the LysoPE enrichment is used to treat inflammatory-diseases of the liver.

7. The method of claim 1, wherein said LysoPE-DOCA-compound is obtainable by coupling lyso-phosphatidyl ethanolamine (LysoPE) to a carboxyl group of ursodeoxycholate (UrsoDOCA) converted into an ester to form a LysoPE-DOCA-compound.

* * * * *